(12) United States Patent
Meconi et al.

(10) Patent No.: US 6,254,558 B1
(45) Date of Patent: Jul. 3, 2001

(54) METHOD FOR PRODUCING A THERAPEUTIC SYSTEM IN THE FORM OF PLASTER

(75) Inventors: Reinhold Meconi, Neuwied; Tina Rademacher, Bad Breisig; Klaus Schumann, Neuwied; Frank Seibertz, Bad Hönningen, all of (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/308,968
(22) PCT Filed: Oct. 10, 1997
(86) PCT No.: PCT/EP97/05608
   § 371 Date: Jul. 15, 1999
   § 102(e) Date: Jul. 15, 1999
(87) PCT Pub. No.: WO98/23266
   PCT Pub. Date: Jun. 4, 1998

(30) Foreign Application Priority Data

Nov. 29, 1996 (DE) ............................................. 196 49 535

(51) Int. Cl.$^7$ ....................................................... A61F 5/00
(52) U.S. Cl. ................................................ 602/6; 424/443
(58) Field of Search .......................... 602/6, 8; 424/443; 607/149

(56) References Cited

U.S. PATENT DOCUMENTS 4,801,458 * 1/1989 Hidaka et al. .

FOREIGN PATENT DOCUMENTS

| 0582727A1 | * | 2/1994 | (EP) . |
| 03 261 721 | | 11/1991 | (JP) . |
| WO 9205811 | | 4/1992 | (WO) . |

* cited by examiner

Primary Examiner—Michael A. Brown
Assistant Examiner—Lalita M. Hamilton
(74) Attorney, Agent, or Firm—D. Peter Hochberg; Katherine R. Vierya; William H. Holt

(57) ABSTRACT

Process for the production, transport and storage of a therapeutic system which is in the form of a plaster and has an active layer supersaturated with active ingredient and containing the active ingredient in homogeneous dispersion or in solution, characterized in that it is carried out avoiding process parameters which favour or induce crystallization of active ingredient, and any type of pressure operating on the plaster and, in particular, on the active layer is avoided while it is carried out.

6 Claims, No Drawings

METHOD FOR PRODUCING A THERAPEUTIC SYSTEM IN THE FORM OF PLASTER

The invention relates to a process for the production, transport and storage of a transdermal therapeutic system (TTS) which is in the form of a plaster and has an active layer supersaturated with active ingredient and containing the active ingredient in homogeneous dispersion or in solution.

Transdermal therapeutic systems normally consist of a backing layer which is impermeable to active and inactive ingredients, of an active ingredient-containing and frequently adhesive reservoir layer and of a protecting layer which is to be removed before application and is likewise impermeable to active ingredient. In order to achieve release of active ingredient sufficient for therapeutic purposes, it may be necessary for the active ingredient-containing layer to be supersaturated with active ingredient. Although such supersaturated transdermal therapeutic systems can have a high thermodynamic activity for therapeutic purposes, on the other hand there is the latent risk that the active ingredients will crystallize completely or partly. It is known that the crystallization of active ingredient is extremely disadvantageous for its release, considerably reducing or completely preventing the latter. It is also known that crystallization of the active ingredient is favoured and/or induced by the operation of pressure on an active ingredient-containing layer.

Transdermal therapeutic systems in the form of plasters are mostly produced by coating the detachable protecting layer with an active ingredient-containing adhesive composition and laminating on the backing layer. The laminate produced in this way and consisting of backing layer, layer supersaturated with active ingredient and removable protecting layer is then wound up, and the broad roll obtained in this way is cut into narrow rolls. It is true that pressure is briefly exerted on the active ingredient-containing layer on carrying out these process steps. However, as a consequence of the short operating time, this operation of pressure has no adverse effect on the crystallization behaviour of the active ingredient in the active ingredient-supersaturated layer. During the subsequent production process, individual plasters are cut out of the narrow rolls described above. For this it is necessary for the laminate to be unwound from the narrow rolls and transported by traction through the machine. This entails use of so-called advance tractions. They grip the laminate from the side and transport it through the machine. During this it is unavoidable that pressure is exerted for a relatively long time on the layer supersaturated in active ingredient, resulting in initiation of crystallization of the active ingredient.

The invention is based on the object of indicating a process for the production, transport and storage of a transdermal therapeutic system in the form of a plaster, by which crystallization of the active ingredient is suppressed.

The object is achieved in a process of the type specified in the precharacterizing clause of claim 1 with the invention by carrying it out avoiding process parameters which favour or induce crystallization of active ingredient, and avoiding any type of pressure operating on the plaster and, in particular, on the active layer while it is carried out.

Surprisingly, it has emerged that crystallization of the active ingredient in the layer supersaturated with active ingredient can be suppressed by avoiding any type of prolonged operation of pressure on the plaster, and, in particular, on the active layer while carrying out the process for the production, transport and storage of a therapeutic system in the form of a plaster. This can be achieved by using reduced pressure to grip the plaster or parts thereof during transport procedures between operational steps in production or packaging. Gripping the plaster or parts thereof with the aid of suction devices avoids any operation of pressure during this. Another possibility for avoiding the operation of pressure is made possible according to the invention on use of gripping or holding devices during or between operational steps for the production, packaging or transport by them taking hold in each case at a distance from the contour of a plaster or of the active layer, for example in the area between separate individual plasters.

Finally, the operation of pressure on the finished plaster during packaging and dispatch to the final distributor is prevented by packaging finished plasters singly in a dimensionally stable pack which has at least limited pressure resistance.

The process according to the invention for the production of transdermal therapeutic systems in the form of plasters of the invention is advantageously and preferably employed for those groups of active ingredients prone to recrystallization in supersaturated phase.

These include active ingredients selected from groups which comprise:
α-adrenoceptor agonists such as, for example, xylometazoline, adrenolone, clonidine, ephedrine, tiamenidine,
β-adrenoceptor agonists such as, for example, formoterol, terbuterol, ritodrine,
α-adrenoceptor blockers such as, for example, dapiperazole, doxazosin, prazosin, yohimbine, trimazosin
β-adrenoceptor blockers such as, for example, acebutolol, atenolol, bisoprolol, bopindolol, bupranolol, propanolol, metoprolol, nadolol, pindolol, timolol,
anabolics such as, for example, androstenediol, bolandiol, clostebol, 4-hydroxy-19-nortestosterone, methenolone,
analgesics (narcotics) such as, for example, alfentanil, buprenorphine, codeine, dimenoxadol, fentanyl, isomethadone, lofentanil, methadone, morphine, morphine derivatives, normethadone, normorphine, propiram, sufentanil, tilidine,
analgesics (non-narcotics) such as, for example, aminopyrine, antipyrine, aspirin, benoxaprofen, bucetin, clometacin, etodolac, felbinac, fenoprofen, flubiprofen, ibufenac, indomethacin, indoprofen, ketoprofen, keterolac, miroprofen,
androgens such as, for example, boldenone, fluoxymesterone, mestanolone, mesterolone, methandrostenolone, 17-methyltestosterone, 17α-methyl-testosterone-3-cyclopentyl enol ether, norethandrolone, normethandrone, oxandrolone, oxymetholone, prasterone, stanolone, stanozolol, testosterone, testosterone 17-chloral hemiacetal, testosterone 17β-cypionate, testosterone enanthate, testosterone nicotinate, testosterone phenylacetate, testosterone propionate, tiomesterone,
anaesthetics such as, for example, amucaine, amylocaine, biphenamine, cocaine, diperodon, ecgonidine, euprocin, fenalcomine, fomocaine, hexobarbital, hexylcaine, hydroxydione, hydroxyprocaine, hydroxytetracaine, ketamine, leucinocaine mesylate, levoxadrol, lidocaine, mepivacaine, meprylcaine, metabutoxycaine, methohexital, midazolam, naepaine, octacaine, orthocaine, oxethazaine, parethoxycaine, phenacaine, piperocaine, polidocanol, pramoxine, prilocaine, procaine, propanocaine, propofol, risocaine, tetracaine, thialbarbital, thiamylal, thiobutabarbital, thiopental, tolycaine, trimecaine, zolamine, antiallergics such as, for example, amlexanox, astemizole, azelastine, cromolyn, fenpiprane, histamine, repirinast, tiaramide, tranilast, traxanox, urushiol, ketotifen, nedocromil, oxatomide, pentigetide antiandrogens such as, for example, bifluranol, Cyoctol, cyproterone, oxendrolone, antianginals such as, for example, amlodipine, amyl nitrite, cinepazet maleate, imolamine, isosorbide dinitrate, limaprost, molsidomine, nitroxyalkylamide derivatives, antiarrhythmics such as, for example, acecainide, adenosine, ajmaline, alprenolol, amoproxan, aprindine, bretylium, tosylate, bubumolol, bunaftine, butidrine, butobendine, meobentine, mexiletine, moricizine, pirmenol, pronethalol, propafenone, pyrinoline, penicillins such as, for example, amdinocillin, pivoxil, amoxicillin, ampicillin, apalcillin, aspoxicillin, azidocillin, azlocillin, bacampicillin, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzyhydrylamine, penicillin G calcium, penicillin G hydrabamine, penicillin N, penicillin O, penicillin V, penicillin V benzathine, penicillin V hydrabamine, penimepicyclin, phenethicillin, piperacillin, pivapicillin, propicillin, quinacillin, sulbenicillin, talampicillin, temocillin, tiacarcillin, antidiabetics such as, for example, sulphonylurea derivatives, acetohexamide, carbutamide, chlorpropamide, glibornuride, gliclazide, glimepiride, glipizide, gliquidone, glisoxepide, glyburide, glybuthiazole, glybuzole, glyhexamide, glymidine, glypinamide, phenbutamide, tolazamide, tolbutamide, tolcyclamide, acarbose, benzylthiazolidine-2,4-dione, calcium mesoxalate, miglitol, antihistaminics such as, for example, acrivastine, bamipine, brompheniramine, chlorpheniramine, dimethindene, metron S, pheniramine, pyrrobutamine, thenaldine, tolpropamine, triprolidine, bietanautine, bromodiphenhydramine, carbinoxamine, clemastine, diphenylpraline, doxylamine, embramine, medrylamine, mephenhydramine, p-methyldiphenhydramine, orphenadrine, phenyltoloxamine, piprinhydrinate, setastine, alloclamide, chloropyramine, chlorothen, histapyrrodine, methafurylene, methaphenilene, methapyrilene, phenbenzamine, pyrilamine, talastine, thenyldiamine, thonzylamine, tripelennamine, zolamine, cetirizine, chlorcyclizine, clocinizine, hydroxyzine, tricyclics, antimigraine agents, hydrogenated ergot alkaloids, β-adrenoreceptor blockers, Ca channel blockers, serotonin antagonists, platelet aggregation inhibitors, antidepressants such as, for example, alpiropride, dihydroergotamine, ergocornine, ercorninine, ergocryptine, ergot, ergotamine, flumedroxone acetate, fonazine, methysergide, oxetorone, pizotyline, sumatriptan, anagrelide, argatroban, cilostazol, daltroban, defibrotide, enoxaparin, Fraxiparin®, indobufen, lamoparan, ozagrel, picotamide, plafibride, tedelparin, ticlopidine, triflusal, bronchodilators such as, for example, ephedrine derivatives such as, for example, albuterol, bambuterol, bitolterol, carbuterol, clenbuterol, chlorprenaline, dioxethedrine, eprozinol, etafedrine, ethylnorepinephrine, fenoterol, hexoprenaline, isoetharine, isoproterenol, mabuterol, metaproterenol, N-methylephedrine, pirbuterol, procaterol, protokylol, reproterol, rimiterol, soterenol, terbutaline, tulobuterol, oestrogens such as, for example, benzestrol, broparoestrol, chlorotrianisene, dienestrol, diethylstilbestrol, diethylstilbestrol dipropionate, dimestrol, fosfestrol, hexestrol, methallenestril, methestrol, colpormon, equilenin, equilin, conjugated oestrogenic hormones, oestrogen esters, estropipate, 17β-0estradiol, estradiol, estradiol benzoate, estradiol 17β-pcypionate, estriol, estrone, ethinyl estradiol, mestranol, moxestrol, mytatrienediol, polyestradiol phosphate, quinestradiol, quinestrol, gestagens such as, for example, allylestrenol, anagestone, chlormadinone acetate, delmadinone acetate, demegestone, desogestrel, dimethisterone, dydrogesterone, ethinylestrenol, ethisterone, ethynodiol, ethynodiol diacetate, flurogestone acetate, gestodene, gestonorone caproate, haloprogesterone, 17-hydroxy-16-methyleneprogesterone, 17α-hydroxyprogesterone, 17α-whydroxygesterone caproate, levonorgestrel, lynestrenol, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, promegestone, quingestrone, trengestone, vasodilators such as, for example, bencyclane, ciclonicate, cinnarizine, citicoline, diisopropylamine dichloroacetate, eburnamonine, fenoxedil, ibudilast, ifenprodil, nafronyl, nicametate, nicergoline, ninodipine, papaverine, pentifylline, tinofedrine, vincamine, vinpocetine, amotriphene, bendazol, benfurodil hemisuccinate, benziodarone, chloracyzine, chromonar, clobenfurol, clonitrate, dilazep, dipyridamole, dropenilamine, efloxate, erythritol, erythrityl tetranitrate, etafenone, floredil, ganglefene, hexestrol bis(β-diethylaminoethyl ether), hexobendine, isosorbide dinitrate, itramin tosylate, khellin, lidoflazine, mannitol hexanitrate, medibazine, nicorandil, pentaerythritol tetranitrate, pentrinitrol, pimefylline, prenylamine, propatyl nitrate, pyridofylline, trapidil, tricromyl, trimetazidine, trolnitrate phosphate, visnadine, bamethan, betahistine, bradykinin, brovincamine, bufeniode, buflomedil, butalamine, cetiedil, ciclonicate, cinepazide, cyclandelate, eledoisin, hepronicate, inositol niacinate, isoxsuprine, kallidin, kallikrein, moxisylyte, nicofuranose, nylidrin, piribedil, suloctidil, xanthinal and niacinate.

What is claimed is:

1. Process for avoiding crystallization of active ingredient from the active layer, which is supersaturated with active ingredient, of a therapeutic system comprising:

avoiding any kind of pressure operating on the therapeutic system which is in the form of a therapeutic plaster during the operational steps of production, packaging, transport and storage.

2. The process of claim 1 wherein the transfer of the therapeutic plaster or of parts thereof is carried out between operational steps in production or packaging by means of sucking action or reduced pressure.

3. The process of claim 1 wherein gripping or holding devices take hold at a distance from the contour of a plaster or the active layer during or between the operational steps of production, packaging or transport.

4. The process of claim 3 wherein the gripping or holding devices take hold in the area between separated individual plasters.

5. The process of claim 1 further comprising packing the finished plasters singly in a dimensionally stable pack with at least limited pressure resistance.

6. Therapeutic systems in the form of plasters having an active layer supersaturated with active ingredient comprising a dimensionally stable pack protecting the plaster so that the layer which is supersaturated with active ingredient is protected from the action of pressure.

\* \* \* \* \*